US008565372B2

(12) United States Patent
Stein et al.

(10) Patent No.: US 8,565,372 B2
(45) Date of Patent: *Oct. 22, 2013

(54) SYSTEM AND METHOD FOR LOW DOSE TOMOSYNTHESIS (75) Inventors: Jay Stein, Boston, MA (US); Andrew Smith, Lexington, MA (US); Zhenxue Jing, Chadds Ford, PA (US); Loren Niklason, Hillsborough, NC (US)

(73) Assignee: Hologic, Inc, Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/397,013

(22) Filed: Mar. 3, 2009

(65) Prior Publication Data
US 2009/0213987 A1 Aug. 27, 2009
US 2012/0263273 A9 Oct. 18, 2012

Related U.S. Application Data (63) Continuation-in-part of application No. 10/723,486, filed on Nov. 26, 2003, now Pat. No. 7,831,296, and a continuation-in-part of application No. 11/791,601, filed as application No. PCT/US2005/042613 on Nov. 23, 2005, now Pat. No. 7,869,563.

(51) Int. Cl.
*G01N 23/083* (2006.01)
*H05G 1/60* (2006.01)
*H05G 1/58* (2006.01)

(52) U.S. Cl.
USPC .............................. 378/37; 378/21; 378/116

(58) Field of Classification Search
USPC ........... 378/21–25, 27, 37, 91, 101, 108–112, 378/114–116
See application file for complete search history.

(56) References Cited

U.S. PATENT DOCUMENTS

| 6,744,848 | B2 * | 6/2004 | Stanton et al. | 378/55 |
| 7,302,031 | B2 * | 11/2007 | Hjarn et al. | 378/37 |
| 7,583,786 | B2 * | 9/2009 | Jing et al. | 378/37 |
| 2001/0038681 | A1 | 11/2001 | Stanton et al. | |
| 2005/0113681 | A1 * | 5/2005 | DeFreitas et al. | 600/426 |
| 2007/0036265 | A1 * | 2/2007 | Jing et al. | 378/37 |

(Continued)

FOREIGN PATENT DOCUMENTS

| EP | 1 759 637 | 3/2007 |
| WO | WO2004/043535 | 5/2004 |
| WO | WO2006/058160 | 6/2006 |

OTHER PUBLICATIONS

International Search Report and Written Opinion from related PCT Application No. PCT/US2009/055981 dated Dec. 8, 2009.
International Search Report and Written Opinion from related PCT Application No. PCT/US2010/026062 dated Apr. 23, 2010.
Wheeler F. W., et al. "Micro-Calcification Detection in Digital Tomosynthesis Mammography" Proceedings of SPIE, Dec. 11, 2001 to Dec. 15, 2001, vol. 6144, Feb. 13, 2006.

(Continued)

*Primary Examiner* — Anastasia Midkiff (57) ABSTRACT

A breast imaging system leverages the combined strengths of two-dimensional and three-dimensional imaging to provide a breast cancer screening with improved sensitivity, specificity and patient dosing. A tomosynthesis system supports the acquisition of three-dimensional images at a dosage lower than that used to acquire a two-dimensional image. The low-dose three-dimensional image may be used for mass detection, while the two-dimensional image may be used for calcification detection. Obtaining tomosynthesis data at low dose provides a number of advantages in addition to mass detection including the reduction in scan time and wear and tear on the x-ray tube. Such an arrangement provides a breast cancer screening system with high sensitivity and specificity and reduced patient dosing.

12 Claims, 7 Drawing Sheets

(56) References Cited

U.S. PATENT DOCUMENTS

| | | |
|---|---|---|
| 2007/0140419 A1* | 6/2007 | Souchay .................. 378/37 |
| 2008/0101537 A1* | 5/2008 | Sendai ..................... 378/23 |
| 2008/0112534 A1 | 5/2008 | Defreitas |
| 2010/0034450 A1* | 2/2010 | Mertelmeier ............ 382/131 |

OTHER PUBLICATIONS

Wu Tao, et al. "Tomographic Mammography Using a Limited Number of Low-Dose Cone-Beam Projection Images" Medical Physics, vol. 30, No. 3, Mar. 1, 2003, p. 365-380.

* cited by examiner

SYSTEM AND METHOD FOR LOW DOSE TOMOSYNTHESIS

RELATED APPLICATIONS

This application is a continuation-in-part and claims priority under 35 U.S.C. 120 to U.S. patent application Ser. No. 11/791,601, which is the National Stage of International Application No. PCT/US2005/042613, filed Nov. 23, 2005, now granted U.S. Pat. No. 7,869,563, and is a continuation in part and claims priority under 35 U.S.C. §120 to patent application Ser. No. 10/723,486, filed Nov. 26, 2003, now granted as U.S. Pat. No. 7,831,296.

FIELD OF THE INVENTION

This application relates to medical imaging and more specifically to a system and method of acquiring low-dose three-dimensional images and using the low dose images in combination with a conventional mammogram to enable improved detection of calcifications and masses with minimal patient dosing.

BACKGROUND

In the U.S. breast cancer mortality is second only to that of lung cancer. Because of its role in early tumor detection, mammography has come are the most commonly used tool for breast cancer screening, diagnosis and evaluation in the United States. A mammogram is an x-ray image of inner breast tissue that is used to visualize normal and abnormal structures within the breasts. Mammograms provide early cancer detection because they can often show a breast lumps and/or calcifications before they are manually palpable.

While screening mammography is recognized as the most effective method for early detection of breast cancer, the modality has limitations. One problem with mammograms lies in their low specificity; that is it is often difficult to determine whether a detected abnormality is associated with a cancerous or benign lesion. The difficulty arises from the fact that a mammogram is two dimensional representations of a three dimensional structure, and overlapping structures in the compressed breast may confound diagnosis.

Efforts to improve the sensitivity and specificity of breast x-rays have included the development of breast tomosynthesis systems. Breast tomosynthesis is a three-dimensional imaging technology that involves acquiring images of a stationary compressed breast at multiple angles during a short scan. The individual images are then reconstructed into a series of thin, high-resolution slices that can be displayed individually or in a dynamic ciné mode.

Reconstructed tomosynthesis slices reduce or eliminate the problems caused by tissue overlap and structure noise in single slice two-dimensional mammography imaging. Digital breast tomosynthesis also offers the possibility of reduced breast compression, improved diagnostic and screening accuracy, fewer recalls, and 3D lesion localization. Examples of breast tomosynthesis systems are described in U.S. Pat. Nos. 7,245,694 and 7,123,684, commonly owned by the Assignee of this application.

One goal of any x-ray imaging system is to obtain the highest quality image while minimizing the patient dose. When selecting a radiation dose to use for imaging, a balance must be attained between image quality and patient safety. As a result an effort has been made to limit the dose of radiation administered during tomosynthesis imaging. For example, the article "Micro-Calcification Detection in Digital Tomosynthesis Mammography", by Wheeler et al. describes that a total patient dosing across tomosynthesis projection images in a single scan should be comparable to that administered during a two view mammography.

SUMMARY OF THE INVENTION

According to one aspect of the invention an improved breast imaging system and method reduces patient dose by leveraging the combined strengths of two-dimensional and three-dimensional imaging. The present invention recognizes that calcification detection should be performed by imaging at a radiation dose sufficient to reduce quantum mottle (essentially image noise caused by photon absorption) to a level which enables viewing of micro-calcifications. However, according to one aspect of the invention it is realized that the resolution needed to view calcifications is not required for viewing masses; rather the problem with accurate mass detection results from structure overlay. Thus three-dimensional imaging at a dose that is considerably less that that used for the 2-D imaging provides sufficient information for improved detection of masses. The combination of the 2D image and low-dose 3D image provides a breast cancer screening system with high sensitivity and specificity.

A tomosynthesis breast imaging system comprising an x-ray source and an x-ray detector, the x-ray source and x-ray detector configurable to acquire a two-dimensional image and a three-dimensional image, wherein the two-dimensional image is acquired at a first dose and the three-dimensional image is acquired at a second dose less than or equal to the first dose.

According to a further aspect of the invention an integrated mammography/tomosynthesis system includes an x-ray source and an x-ray detector, the x-ray source and x-ray detector configurable to acquire at least one of a mammogram and a set of tomosynthesis images, wherein the mammogram is acquired at a first dosage and the set of tomosynthesis images are acquired at a second dosage less than or equal to the first dosage.

According to another aspect of the invention, a method of imaging a breast including the step of acquiring a three-dimensional image of the breast using a lower dosage than used to acquire a two-dimensional image of the breast.

A method of imaging a breast including the steps of acquiring a low-dose three-dimensional image of the breast, acquiring a two-dimensional image of the breast using a dose corresponding to a mammogram imaging dose, using the conventional dose mammogram to locate calcifications in the breast and using the low-dose three-dimensional image to locate masses in the breast.

According to further aspect of the invention, a method of imaging a breast includes the steps of acquiring a two-dimensional image of a breast using a first x-ray dose, acquiring a three-dimensional image of the breast using a second x-ray dose less than the first x-ray dose and using the two-dimensional image and three-dimensional image to identify calcifications and masses in the breast.

In describing examples and preferred embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

DETAILED DESCRIPTION

Sensitivity is the ability of the imaging technology to detect a cancerous lesion. Specificity is the ability of the imaging technology to ignore artifacts in images which merely appear similar to lesions. The present invention leverages the combined strengths of two-dimensional and three-dimensional imaging to provide a breast imaging system with improved sensitivity, specificity and the added advantage of reduced patient dosing.

One important characteristic of any digital imaging system is the ability to vary the amount and intensity of radiation used to generate any image. Radiation intensity is related to the atomic number (Z) of the x-ray target, the x-ray current (mA), x-ray voltage and x-ray beam filtration. Radiation intensity is varied to improve image quality, which in turn improves diagnostic sensitivity. When radiation intensity increases, quantum mottle (image noise caused by photon absorption) will decrease and visa versa.

Radiation intensity is directly related to patient dosage. The greater the intensity of radiation, the higher the x-ray dose to the patient. Much effort has been put into the design of mammography systems capable of acquiring a quality image at a lowest possible dosage. In the current full field digital mammography systems, the average mammogram dose is 1.2-1.5 mGy.

Many mammography and tomosynthesis systems allow the operator to control x-ray exposure by manually setting technique factors such as mA and mSec. Some systems include Automatic Exposure Control (AEC) functionality which control a duration of administration of radiation, turning off the x-ray source when the desired dose has been administered. Automatic Exposure Control (AEC) methods may vary the dosing parameters, including exposure time, kV, mA and filter modes for an image to vary the exposure and the radiation intensity. According to one aspect of the invention, AEC functionality of a tomosynthesis system may be used to reduce the dosage applied during a tomosynthesis scan, for example by changing any one of the above dosing parameters.

Alternatively (or in addition) the dosage may be controlled by limiting the angle of the scan and or the number of projection images obtained during a scan. The scan angle and number of projection images may also be controlled via a user interface located on the gantry or at the radiologists workstation.

In one embodiment, the sum of the dose administered during acquisition of all of the projection images (i.e., the tomosynthesis dose) is less than equal to the dose of a conventional mammogram. For example the tomosynthesis dose may be in the range of 0.25 to 1.0 of the dose used to acquire a single view of a conventional mammogram. In an exemplary embodiment it has been determined that sufficient information for calcification and mass detection may be obtained using a conventional mammogram view acquired with a dose of 1.0-1.5 mGy and a three-dimensional image reconstructed from fifteen projection images taken at a total dose of 0.6 mGy. In an alternate embodiment, the total dose of 0.6 mGy may be administered from projection images obtained by performing an angular scan over 7°, and obtaining, for example, 7 projection images. Such an arrangement allows the three-dimensional data to be obtained at a lower dose and faster scan time. An additional advantage of low-dose tomosynthesis acquisition is that it increases the longevity of the x-ray tube.

FIGS. 1-6 illustrate a non-limiting example of a multi-mode mammography/tomosynthesis system embodying the present invention. The system comprises a gantry 100 and a data acquisition work-station 102. Gantry 100 includes a housing 104 supporting a tube arm assembly 106 rotatably mounted thereon to pivot about a horizontal axis 402 (FIG. 4) and carrying an x-ray tube assembly 108. X-ray tube assembly 108 includes (1) an x-ray tube generating x-ray energy in a selected range, such as 20-50 kV, at mAs such as in the range 3-400 mAs, with focal spots such as a nominal size 0.3 mm large spot and nominal size 0.1 mm small spot (2) supports for multiple filters such as molybdenum, rhodium, aluminum, copper, and tin filters, and (3) an adjustable collimation assembly selectively collimating the x-ray beam from the focal spot in a range such as from 7.times.8 cm to 24.times.29 when measured at the image plane of an x-ray image receptor included in the system, at a maximum source-image distance such as 75 cm. Also mounted on housing 104, for rotation about the same axis 402, is a compression arm assembly 110 that comprises a compression plate 122 and a receptor housing 114 having an upper surface 116 serving as a breast plate and enclosing a detector subsystem system 117 comprising a flat panel x-ray receptor 502 (FIG. 5), a retractable anti-scatter grid 504 and a mechanism 506 for driving and retracting anti-scatter grid 504. Housing 104 also encloses the following components schematically illustrated in FIG. 4: a vertical travel assembly 404 for moving tube arm assembly 106 and compression aim assembly 110 up and down to accommodate a particular patient or imaging position, a tube arm assembly rotation mechanism 406 to rotate tube arm assembly 106 about axis 402 for different imaging positions, a detector subsystem rotation mechanism 408 for rotating components of detector subsystem 117 (such as x-ray receptor 502) about axis 402 to accommodate different operations modes, and couple/uncouple mechanism 410 to selectively couple or uncouple tube arm assembly 106 and compression arm assembly 110 to and from each other, and tube arm assembly 106 and detector subsystem 117 to and from each other. Housing 104 also encloses suitable motors and electrical and mechanical components and connections to implement the functions discussed here. A patient shield 200, schematically illustrated in FIG. 2, can be secured to compression arm assembly 110 to provide a mechanical interlock against patient contact with the rotating x-ray tube arm assembly 106. Work-station 102 comprises components similar to those in the Selenia™ mammography system, including a display screen (typically a flat panel display that may include touch-screen functionality), user interface devices such as a keyboard, possibly a touch-screen, and a mouse or trackball, and various switches and indicator lights and/or displays. Work-station 102 also includes computer facilities similar to those of the Selenia™ system (but adapted through hardware, firmware and software differences) for controlling gantry 100 and for processing, storing and displaying data received from gantry 100. A power generation facility for x-ray tube assembly 108 may be included in housing 104 or in work-station 102. A power source 118 powers work-station 102. Gantry 100 and work-station 102 exchange data and controls over a schematically illustrated connection 120.

Figure 6:
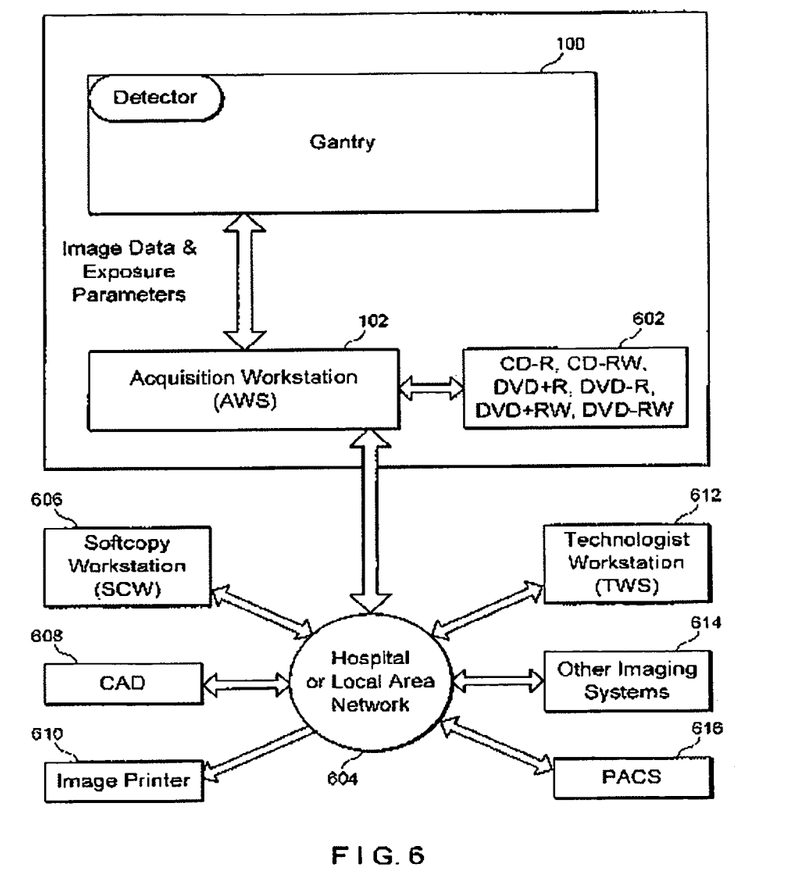
FIG. 6 is a block diagram of the disclosed system when connected to other systems.

As illustrated in FIG. 6, additional storage facilities 602 can be connected to work-station 102, such as one or more optical disc drives for storing information such as images and/or for providing information to work-station 102 such as previously obtained images and software, or a local printer (not shown). In addition, the disclosed system can be connected to a hospital or local area or other network 604, and through the network to other systems such as a soft copy workstation 606, a CAD (Computer Aided Detection) station 608 for computer-processing mammography and/or tomosynthesis images to identify likely abnormalities, an image printer 610 for printing images, a technologist workstation 612, other imaging systems 614 such as other mammography systems or systems for other modalities for exchange of images and/or other information, and to a PACS (Picture Archiving) systems 616 for archiving images and other information and/or retrieving images and other information.

Figure 1:
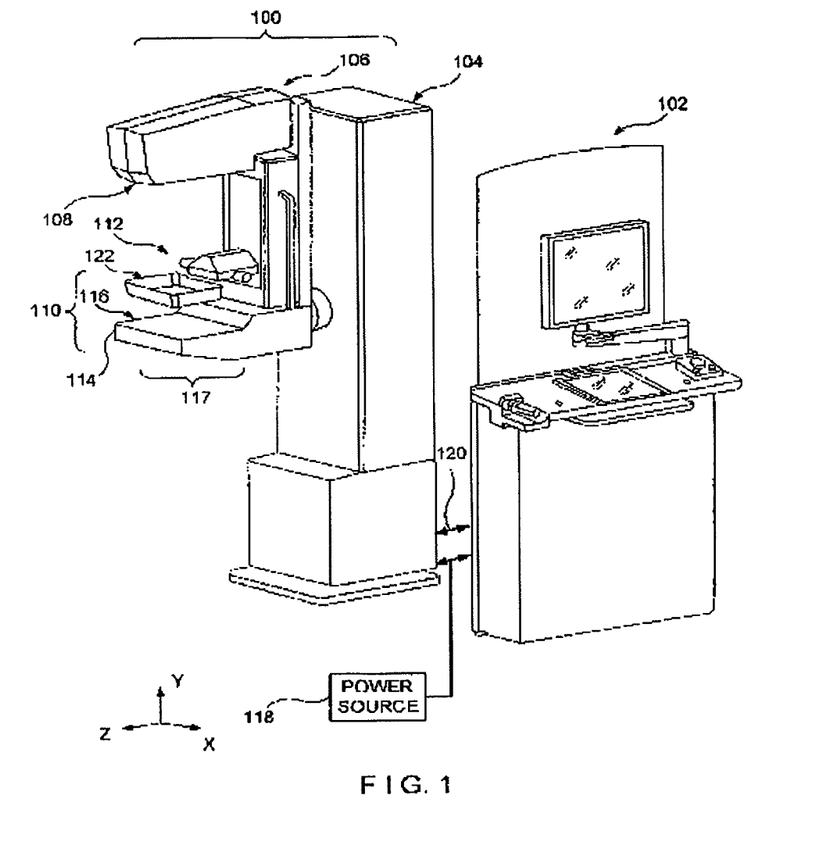
FIG. 1 is a perspective view of a gantry and an acquisition workstation in accordance with an example of the disclosed system.

In standard mammography mode, typically used for screening mammography, tube arm assembly 106 and compression arm assembly 110 are coupled and locked together by 410 in a relative position such as seen in FIG. 1, such that an x-ray beam from x-ray tube assembly 108 illuminates x-ray receptor 502 when the patient's breast is compressed by compression device 112. In this mode, the system operates in a manner similar to said Selenia™ system to take a mammogram. Vertical travel assembly 404 and tube arm rotation mechanism 406 can make vertical adjustments to accommodate a patient, and can rotate tube arm assembly 106 and compression arm assembly 10 together as a unit about axis 402 for different image orientations such as for CC and for MLO images. For example, tube arm assembly 106 and compression arm assembly 110 can rotate between (−195.degree.) and (+150.degree.) about axis 402. As in the Selenia™ system, compression device 112 includes a compression paddle 122 that can move laterally, in a direction along the chest wall of a patient, to adjust for different imaging orientations. However, as described further below, the mechanism for supporting and moving compression paddle 122 is different. Typically, anti-scatter grid 504 is over x-ray receptor 502 in the standard mammography mode to reduce the effect of x-ray scatter.

Figure 2:
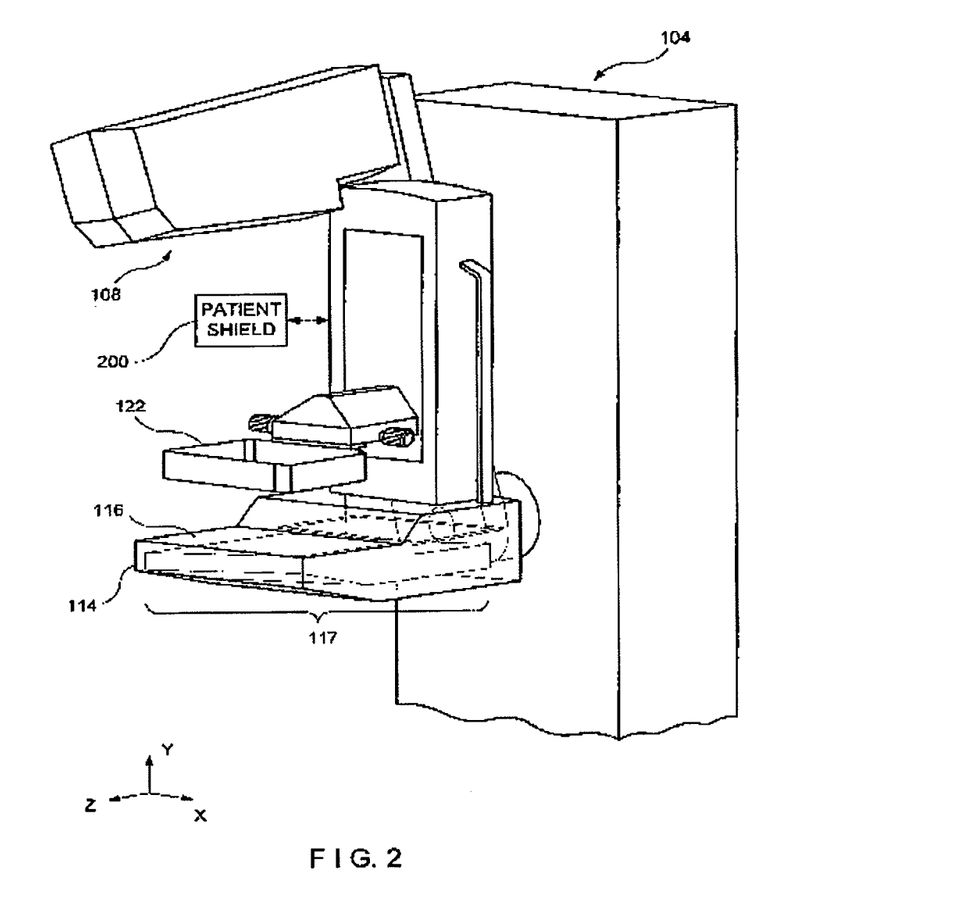
FIG. 2 is an enlarged view of a portion of the system of FIG. 1, with a tube arm assembly in a rotated position.

In tomosynthesis mode, tube arm assembly 106 and compression arm assembly 110 are decoupled by unit 410 such that compression arm assembly 110 stays in one position, compressing the patient's breast, while tube arm assembly 106 rotates about axis 402, for example between the position illustrated in FIG. 2 to that illustrated in FIG. 11, or .+−.15.degree. relative to compression arm assembly 10. Tomosynthesis can be carried out for different image orientations, so that compression arm assembly 10 can be rotated about axis 402 (alone or together with assembly 106) for a desired image orientation and locked in place, and then tube arm assembly 106 can be rotated relative to that position of compression arm assembly 110 for tomosynthesis imaging over .+−.15.degree. or some other desired angular range. For example, low dose tomosynthesis may be performed over a seven degree angular range to collect in the area of seven projection images.

Figure 3:
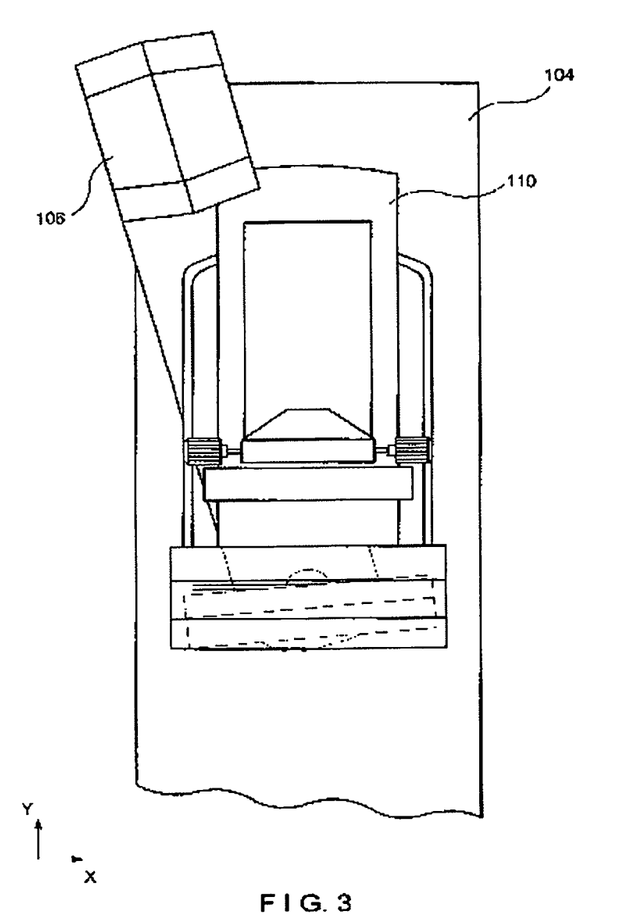
FIG. 3 is a front elevation of the apparatus of FIG. 2.
Figure 4:
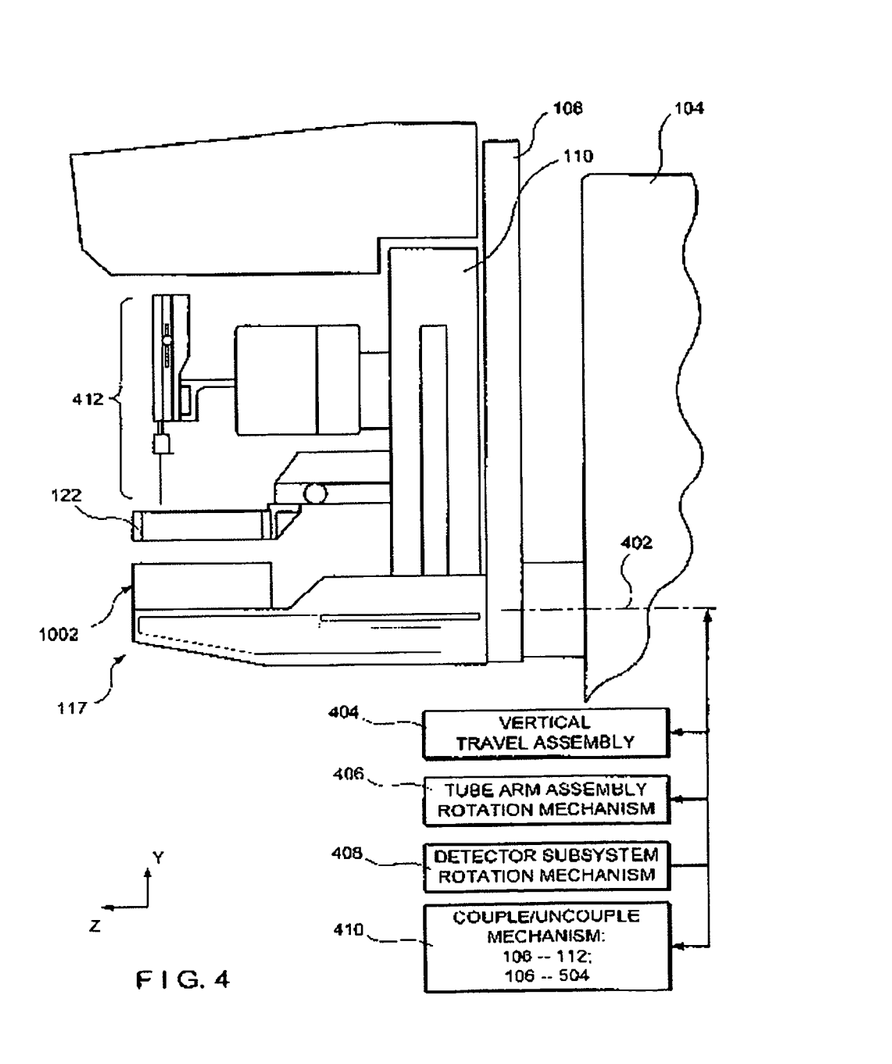
FIG. 4 is a side view of a gantry with a biopsy station and a spacer, with schematic illustration of other mechanisms.
Figure 5:
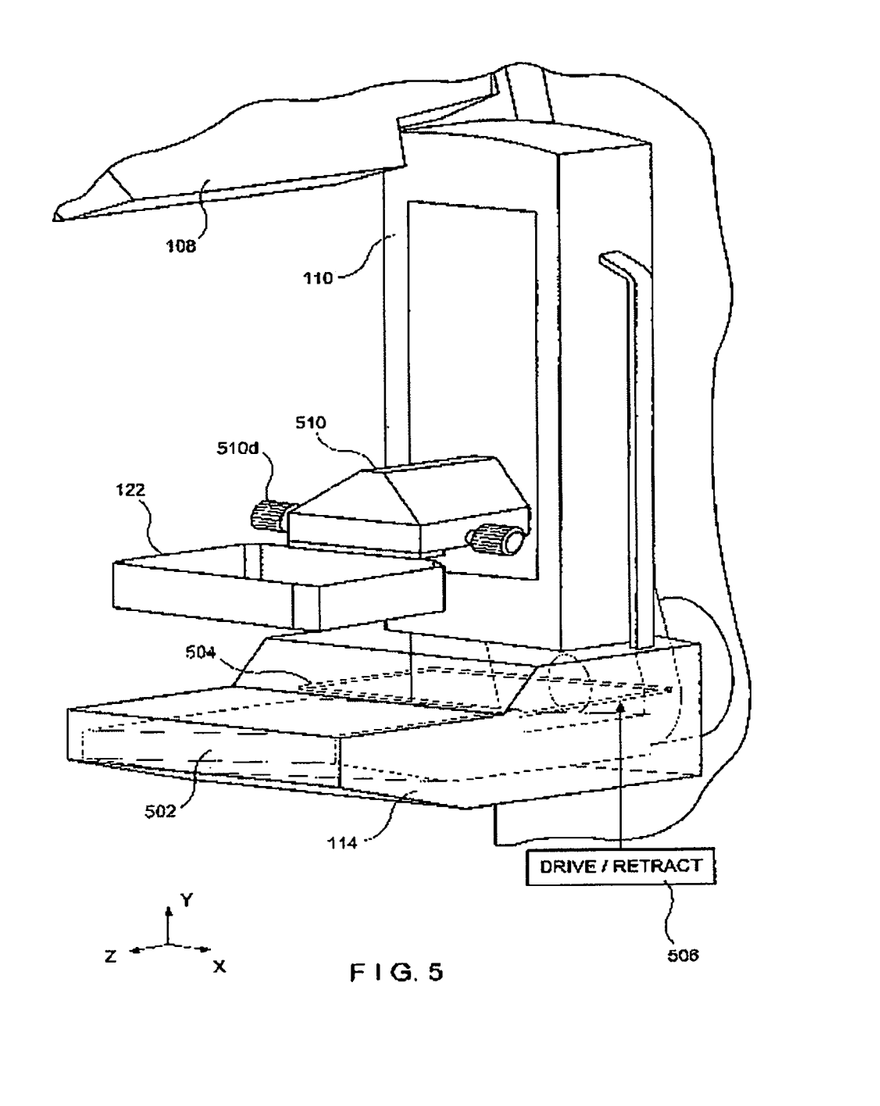
FIG. 5 is an enlarged view of a portion of FIG. 1.

In one example, 11 images are taken during an angular sweep of tube arm assembly 106, one every approximately 3.degree. However, a different number of images can be taken, for example up to 21 during a single sweep. For tomosynthesis images, the x-ray tube in x-ray tube assembly 108 continuously rotates and the x-ray tube is pulsed for each image, for example, for x-ray energy pulses each lasting approximately 100 mSec, although pulses of different duration can be selected. Alternatively, the rotational motion can stop for taking each image, or continuous motion without pulsing can be used (and the timing of data measurements relied to define pixel values). As seen in FIGS. 2, 3, and 5, in this mode mechanism 506 fully retracts anti-scatter grid 504 away from x-ray receptor 502 so grid 504 is out of the image. Also as seen in these Figs., while the breast remains immobilized in compression arm assembly 110 during the angular sweep of tube arm assembly 106, x-ray receptor 502 rocks within receptor housing 114. In this rocking motion, controlled by unit 408 (FIG. 4), a line normal to the image face of x-ray receptor 502 may keep pointing to the focal spot of the x-ray tube in x-ray tube assembly 108. Alternatively, the rotation of tube arm assembly 106 and rocking of x-ray receptor 502 can be through different angles; for example, tube arm assembly 106 can rotate through 15.degree. while x-ray receptor 502 rocks through 5.degree., i.e. the rocking angle can be an amount one-third that of assembly 108. Synchronous rotation of tube arm assembly 106 and rocking of x-ray receptor 502 can be achieved by controlling separate motors for each or, alternatively, through using a motor to drive tube arm assembly 106 and a mechanical coupling between the rotation of tube arm assembly 106 and rocking of x-ray receptor 502.

Image data can be obtained and processed into tomosynthesis images for display and/or storage as described in the material incorporated by reference, for example in co-pending patent application Ser. No. 10/723,486 or in U.S. Provisional Application No. 60/628,516, filed Nov. 15, 2004.

In a combination mode, during a single compression of the patient's breast the system takes a conventional mammogram and tomosynthesis images. In this mode, while the breast remains compressed in compression arm assembly 110, (1) tube arm assembly 106 sweeps and x-ray receptor 502 rocks, each through an appropriate angle, and exposures are taken for tomosynthesis images, and (2) a standard mammogram is taken. The standard mammogram can be taken at a 0.degree. relative angle between tube arm assembly 106 and a normal to the imaging plane of x-ray receptor 502, and can be taken before or after the tomosynthesis images are taken or between the taking of two successive tomosynthesis images. Typically, each tomosynthesis image utilizes substantially lower x-ray dose than the standard mammogram.

For example, as described above, the total dosage of all projection images taken during the tomosynthesis scan can range from 0.25 to 1.0 times that of a single dose of a mammogram. The relationship between the two dosages can be user-selected to control any one of the x-ray tube voltage, current, tomosynthesis scan angle, number of projection images obtained, etc. In alternate embodiments, the dosage may be altered via a simple switch on the gantry, or view a user control at a radiologist workstation. In still alternate embodiments the dosage may vary automatically as the radiologist switches between modes.

Figure 7:
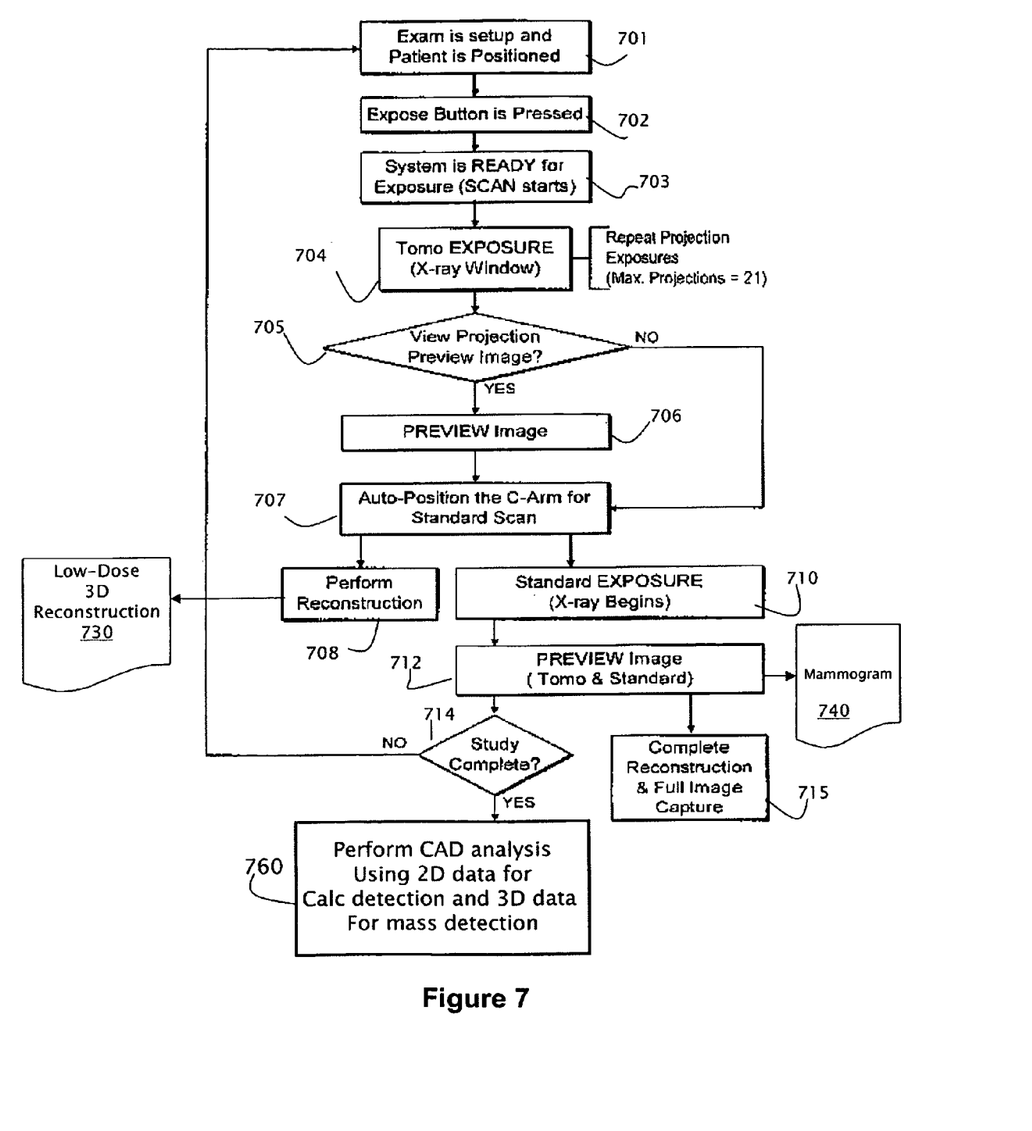
FIG. 7 is a flow chart illustrating one of several examples of work flow for a combination mode.

FIG. 7 illustrates an example of workflow for performing mammography and tomosynthesis in a combination mode. At step 701 the system is set for a tomosynthesis scan, and the required dosage is either input manually or updated automatically in response to a selected mode of operation. During steps 702-708 the low dose tomosynthesis image 730 is acquired. During steps 710-715 the mammogram 740 is acquired. At step 760, CAD is performed using the 2D image for calc detection and the 3D image for mass detection.

Again, these are examples, and different steps or orders of steps can be used instead. For example, a preferred approach may be to take the standard mammogram first, then move arm 106 to one end of its rotational range for tomosynthesis and take the tomosynthesis images. The order in which the two types of images are taken may be optimized such that the overall imaging time is minimized, and an order that achieves such minimization can be the preferred order. The exposure (tube current mA, tube voltage kVp, and exposure length msec) techniques for the standard mammogram and the tomosynthesis exposures can be set manually, or by using automatic methods. If the standard mammogram is taken first, its exposure techniques can be used to set an optimal technique for the subsequent tomosynthesis images, and vice versa. The exposure technique can be modified dynamically, if the software senses that the signal reaching the image receptor is either too low or too high and adjust subsequent exposures as needed.

Although the above has described the use of the present invention with regard to a system which supports acquisition of both tomosynthesis and mammogram images, the present invention is not limited to an integrated multi-mode system but may also be used in any system that is capable of performing tomosynthesis. For example the present invention may be used in a system which includes only tomosynthesis imaging capability. Such systems may use a legacy mammogram for example for calcification detection, or may obtain a single tomosynthesis image at higher dosage to use as their 2D image. In addition, the present invention may be used in any system which incorporates tomosynthesis imaging capability with a different modality, such as molecular breast imaging or ultrasound imaging. In short any breast imaging systems which includes tomosynthesis imaging capabilities falls within the scope of the present invention.

The above specific examples and embodiments are illustrative, and many variations can be introduced on these examples and embodiments without departing from the spirit of the disclosure or from the scope of the appended claims. For example, elements and/or features of different illustrative embodiments may be combined with each other and/or substituted for each other within the scope of this disclosure and appended claims.

The invention claimed is:

1. A tomosynthesis breast imaging system comprising:
   an x-ray source configured to move along an arc; and
   an x-ray detector;
   wherein the x-ray source and x-ray detector are configured to acquire a two-dimensional image and a three-dimensional image, wherein the two-dimensional image is acquired at a first dose and the three-dimensional image is acquired at a second dose less than or equal to the first dose, and wherein acquisition of the two-dimensional image is separate from acquisition of the three-dimensional image such that the x-ray source moves along the arc for the acquisition of the three-dimensional image.

2. The tomosynthesis breast imaging system of claim 1 wherein the second dose is a multiple of 0.25 to 1.0 of the first dose.

3. The tomosynthesis breast imaging system of claim 1 wherein the second dose is a multiple of 0.25 to 0.75 of the first dose.

4. The tomosynthesis breast imaging system of claim 1 wherein the second dose is half of the first dose.

5. The tomosynthesis breast imaging system of claim 1 wherein the first and second dose are controlled by varying at least one of a voltage, current, filter and exposure time of the x-ray source.

6. The tomosynthesis breast imaging system of claim 1 wherein the first and second dose are controlled by varying at least one of a scan angle and a number of projection images of a tomosynthesis exposure.

7. The tomosynthesis breast imaging system of claim 1 wherein the first and second dose are selected according to a mode of operation of the tomosynthesis breast imaging system.

8. An integrated mammography/tomosynthesis breast imaging system comprising:
   an x-ray source; and
   an x-ray detector;
   wherein the x-ray source and x-ray detector are configured to acquire a mammogram and a plurality of tomosynthesis projection images, wherein the plurality of tomosynthesis projection images are acquired at a tomosynthesis dose that is less than a mammogram dose used to acquire the mammogram, and wherein acquisition of the mammogram is separate from acquisition of the plurality of tomosynthesis projection images such that the x-ray source moves along the arc for the acquisition of the plurality of tomosynthesis projection images.

9. A method of imaging a breast including the steps of: acquiring a two-dimensional image of a breast using a first x-ray dose, acquiring a three-dimensional image of the breast using a second x-ray dose less than the first x-ray dose and using the two-dimensional image and three-dimensional image to identify calcifications and masses in the breast, wherein acquisition of the two-dimensional image is separate from acquisition of the three-dimensional image.

10. A method of imaging a breast in a breast imaging system capable of generating two-dimensional images and three-dimensional images, including the steps of:
   in response to an input selecting acquisition of a three-dimensional image, acquiring the three-dimensional image including the step of controlling an x-ray dosage administered during the acquisition of the three-dimensional image so that the x-ray dosage is less than a dosage used to acquire a two-dimensional image, wherein acquisition of the two-dimensional image is separate from acquisition of the three-dimensional image.

11. The method of step 12 wherein the step of controlling adjusts at least one of an x-ray voltage, x-ray current and x-ray filter.

12. The method of step 12 wherein the step of controlling adjusts at least one of an angle of a tomosynthesis scan and a number of projection images of the tomosynthesis scan.

* * * * *